United States Patent [19]
Altman

[11] Patent Number: 5,545,183
[45] Date of Patent: Aug. 13, 1996

[54] METHOD AND APPARATUS FOR DELIVERING DEFIBRILLATION THERAPY THROUGH A SENSING ELECTRODE

[75] Inventor: Peter A. Altman, San Francisco, Calif.

[73] Assignee: Ventritex, Inc., Sunnyvale, Calif.

[21] Appl. No.: 351,864

[22] Filed: Dec. 7, 1994

[51] Int. Cl.⁶ .................................................. A61N 1/39
[52] U.S. Cl. ...................................... 607/5; 607/4
[58] Field of Search ...................... 607/4, 122, 5

[56] References Cited

U.S. PATENT DOCUMENTS

| | | | |
|---|---|---|---|
| 5,014,696 | 5/1991 | Mehra | 128/419 |
| 5,193,535 | 3/1993 | Bardy et al. | 607/4 |
| 5,325,870 | 7/1994 | Kroll et al. | 607/122 |
| 5,336,253 | 8/1994 | Gordon et al. | 607/122 |
| 5,342,414 | 8/1994 | Mehra | 607/127 |
| 5,431,681 | 7/1995 | Helland | 607/4 |

*Primary Examiner*—William E. Kamm
*Attorney, Agent, or Firm*—Steven M. Mitchell; M. Elizabeth Bush; Mark J. Meltzer

[57] ABSTRACT

A pulse generator circuit and method for using a defibrillation lead positioned close to the right ventricular apex to optimize energy delivery and sensing. This method includes operating a defibrillator-pacemaker system in a true bipolar sensing mode as long as high voltage therapy is not required. When required, the defibrillator-pacemaker system delivers a first high voltage therapy via an RV defibrillation electrode, and, using true bipolar sensing, determines whether the first high voltage therapy was successful. If the first high voltage therapy is deemed to be successful, then true bipolar sensing is resumed. Otherwise, the defibrillator-pacemaker system causes a ring electrode to be electrically connected to the RV defibrillation electrode, delivers a second high voltage therapy, and, using integrated bipolar sensing determines whether the second high voltage therapy was successful. In this way, because no new circuit elements are added within the lead, the lead size and complexity are not increased.

17 Claims, 7 Drawing Sheets

METHOD AND APPARATUS FOR DELIVERING DEFIBRILLATION THERAPY THROUGH A SENSING ELECTRODE

FIELD OF THE INVENTION

The present invention relates in general to medical devices, and it more particularly relates to a lead switching matrix for use in an implantable cardiac pulse generator for the detection and management of cardiac arrhythmias. The invention more specifically relates to a method for activating a true bipolar sense electrode to deliver high voltage defibrillation therapies.

BACKGROUND OF THE INVENTION

In recent years there has been a great deal of interest and progress in the integration of implantable medical devices such as defibrillators and pacemakers. For the purpose of this application, "defibrillation" is used in a broad sense, as including the application of relatively high energy and high voltage shocks to the heart to terminate tachyarrhythmias including fibrillation and malignant tachycardias. Similarly, "pacing" is used in a broad sense, as including the application of relatively low energy and low voltage pacing pulses to maintain an adequate heart rate or to break a tachycardia by stimulating the patient's heart. One traditional approach to combining pacing and true bipolar sensing electrodes in a defibrillation lead is to provide a ring electrode located between the pacing tip electrode and the defibrillation electrode where the ring electrode is dedicated exclusively to sensing the heart's electrical activities. The space required for this ring electrode forces the defibrillation electrode to be set back from the RV apex, and, because of the size limitations of the right ventricle, decreases the length available for the defibrillation electrode.

However, in the context of endocardial ventricular leads, it would be desirable to provide an electrode, or electrode pair, for sensing adjacent the ventricular apex, while still providing an electrode which also is located as close to the apex as possible.

Exemplary attempts to accomplish such objective are described in U.S. Pat. No. 5,336,253, to Gordon et al., and U.S. Pat. No. 5,342,414 to Mehra, both of which are incorporated herein by reference in their entirety. The Gordon patent describes a combined pacing and cardioversion lead system with internal electrical switching components for unipolar or bipolar sensing of electrograms, pacing at normal pacing voltages and cardioversion or defibrillation. In bipolar embodiments, a ring electrode is coupled through the internal switching circuitry to a large surface area cardioversion electrode. In these embodiments, pacing and sensing are accomplished through a pair of conductors extending through the lead body to the tip and ring electrodes. When cardioversion shocks are delivered to the ring electrode, cardioversion energy is also directed to the cardioversion electrode through the operation of the switching circuitry in response to the magnitude of the applied cardioversion pulse.

However, the lead system disclosed in the Gordon patent uses discrete and non-programmable internal switching components, such as the zener diodes in the arrangement of FIG. 3, or the surge suppressor and the resistor in the arrangement of FIG. 4. These internal switching components appear to indiscriminately and automatically connect the ring electrode to the cardioversion electrode upon the application of a cardioversion pulse exceeding a predetermined magnitude. As a result, the lead system described in this patent lacks the required flexibility to adapt the application of the cardioversion shocks to specific cardioversion conditions in progress.

Wherefore, it would be highly desirable to have a new lead switching matrix for use in an implantable cardiac stimulator for the detection and management of cardiac arrhythmias. It would also be desirable to have a new method for activating a true bipolar sense electrode to deliver high voltage therapies.

The transvenous defibrillation lead described in the Mehra patent is directed towards optimizing the size, spacing and location of the electrodes, and more specifically towards providing a bipolar sensing pair of electrodes having adequate interelectrode spacing to insure appropriate sensing of cardiac depolarization, while still allowing the placement of the electrode as close to the distal end of the lead body as possible. The lead includes a helical electrode, extending distally from the lead body, for use as the active electrode in cardiac pacing and for use in sensing cardiac depolarizations. A ring tip electrode or a cylindrical ring electrode is located at or adjacent to the distal end of the lead body and provides the second electrode for use in sensing depolarizations. The helical electrode is insulated from the point it exits the lead body until a point adjacent to its distal end. The defibrillation electrode is mounted with its distal end closely adjacent to the distal end of the lead body, such that its distal end point is within one centimeter of the distal end of the lead body.

The leads described in the foregoing Gordon and Mehra patents do not provide for integrated bipolar sensing, wherein sensing is carried out between the cardioversion electrode and the tip electrode. One feature that distinguishes integrated bipolar sensing and true bipolar sensing is that integrated bipolar sensing lacks an electrode dedicated solely to bipolar sensing in conjunction with the pacing tip. Typically, in an integrated bipolar electrode, the same electrode used for bipolar sensing in conjunction with the pacing tip is used to deliver defibrillation or cardioversion therapies. There are two potential problems with integrated bipolar electrodes. First, because the integrated electrode must be large for efficient delivery of defibrillation or cardioversion energy, it may reduce the resolution of the sensed signal due to spatial averaging of the different potentials within the heart. Secondly, the integrated electrode serves also as a defibrillation electrode and is likely to have substantial residual charge at its interface after a defibrillation therapy pulse. The residual charge or polarization of the electrodes results in less accurate sensing immediately after therapy. The true bipolar sense electrode should not be subject to these potential problems. The size of the true bipolar electrode is not governed by the need for efficient energy delivery during therapy and can be optimized for sensing. Additionally, because a negligible current flows across the electrode tissue interface, there is no build-up of charge or polarization at the interface, enabling the accurate measurement of endocardial signals immediately following therapy. However, a drawback with true bipolar sensing exists because the sense electrode in a true bipolar lead is located adjacent to the pacing electrode, and thus the cardioversion electrode is generally positioned further away from the apex of the heart, thus disadvantageously reducing the delivered therapeutic energy.

Therefore, it would be desirable to have a new lead which permits the optimal delivery of defibrillation and cardioversion energies, and the minimization of poor sensing due to polarization effect. It would also be desirable to optimize the electrode functionality without the complexity and dimensional constraints of circuit elements located within the lead.

SUMMARY OF THE INVENTION

The present invention is directed towards providing a method and apparatus for using a defibrillation lead to defibrillate and sense in close proximity to the heart ventricular apex. In particular, the invention is directed towards providing a new method which permits the optimal delivery of defibrillation and cardioversion energies, and the minimization of poor sensing due to polarization effect, without the complexity and dimensional constraints of circuit elements located within the lead.

It is also an object of the present invention to provide a method for activating a true bipolar sense electrode to deliver high voltage therapies, while simultaneously allowing for the flexible application of these therapies to a particular arrhythmia condition in progress.

Briefly, the foregoing and other objects of the present invention are realized by providing a new method for operating a defibrillator-pacemaker system in a true bipolar sensing mode as long as high voltage therapy is not required. When required, the defibrillator-pacemaker system delivers a first high voltage therapy via an RV defibrillation electrode, and, using true bipolar sensing, determines whether the first high voltage therapy was successful. If the first high voltage therapy is deemed to be successful, then true bipolar sensing is resumed. Otherwise, the defibrillator-pacemaker system causes a ring electrode to be electrically connected to the RV defibrillation electrode, delivers a second high voltage therapy, and, using integrated bipolar sensing determines whether the second high voltage therapy was successful.

If the second high voltage therapy is determined to be successful, then the defibrillator-pacemaker system resumes true bipolar sensing. Otherwise, a third high voltage therapy is delivered, and a determination is made, using integrated bipolar sensing, as to whether this third high voltage therapy was successful. If it is determined that this therapy was not successful, then another high voltage therapy is delivered, and the routine of inquiring about the success of the therapy, delivering a high voltage therapy and conducting integrated bipolar sensing is repeated as many times as necessary. If, on the other hand, it is determined that the high voltage therapy was successful, then the defibrillator-pacemaker system switches back to, and resumes true bipolar sensing. It may alternatively be desirable to deliver a first defibrillation shock with the ring electrode electrically connected to the RV defibrillation electrode and/or to switch back to the true bipolar sensing configuration following delivery of the defibrillation shock(s).

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION

Figure 1:
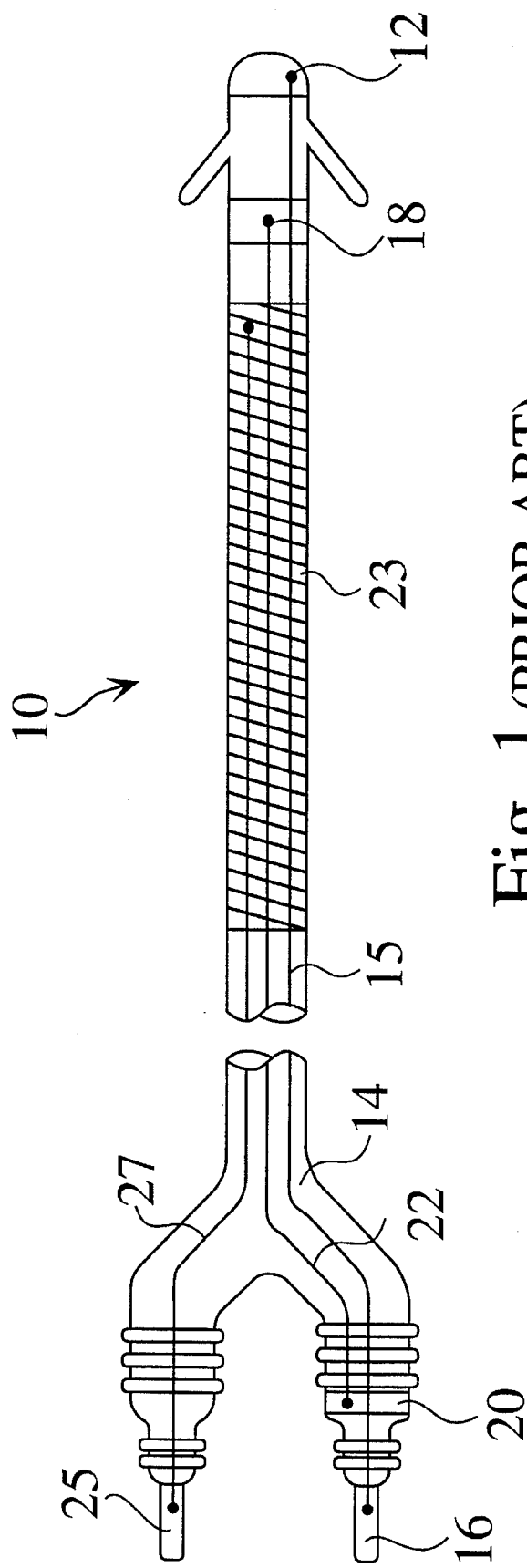
FIG. 1 is a schematic view of a conventional lead which can be used with a switching matrix of the present invention.

FIG. 1 (Prior Art) schematically illustrates one traditional approach to combining pacing and true bipolar sensing electrodes to defibrillation leads. The lead 10 is a right ventricular (RV) transvenous defibrillation lead with true bipolar sensing, whereby a bipolar electrode is dedicated exclusively for sensing the heart's electrical activities. Lead 10 includes a tip electrode 12 mounted at the distal end of an insulative lead body 14, and coupled to a conductor 15, which, in turn, is electrically connected to a connector 16.

Lead 10 further includes an indifferent sense electrode which is typically a ring electrode 18 surrounding lead body 14, a short distance from tip electrode 12. Ring electrode 18 forms a true bipolar sensing electrode pair with tip electrode 12, and is coupled to a connector 20 through a conductor 22.

An elongated large surface area defibrillation or cardioversion electrode 23 is coupled to a connector 25 through a conductor 27. Electrode 23 takes the shape of a space wound coil, wrapped around insulative lead body 14, ,and extends for a preset axial distance therealong. This axial distance is selected such that the proximal end of electrode 23 generally terminates in the vicinity of the tricuspid valve when the distal tip of lead 10 is secured to the myocardium of the RV apex. The distal end of electrode 23 is closely positioned relative to ring electrode 18. Connectors 16, 20 and 25 allow the coupling of lead 10 to an implanted pulse generator.

In operation, bipolar sensing and pacing may take place between tip electrode 12 and ring electrode 18 through conductors 15 and 22, respectively. When cardioversion shocks are delivered, connector 25 which is coupled to one of the output terminals of a cardioversion pulse generator transmits the cardioversion therapy in a shock or pulse form. The shock is delivered to the myocardial cells via electrode 23 and an indifferent electrode or a plurality of indifferent electrodes (not shown) such as a coil electrode located in the superior vena cava (SVC), an epicardial patch electrode positioned in the left chest wall, the pulse generator housing implanted in the lea pectoral region, or a combination of these.

However, in the context of endocardial ventricular leads, it would be desirable to provide an electrode, or electrode pair, for sensing adjacent the ventricular apex, while still providing an electrode which also is located as close to the apex as possible.

Figure 2:
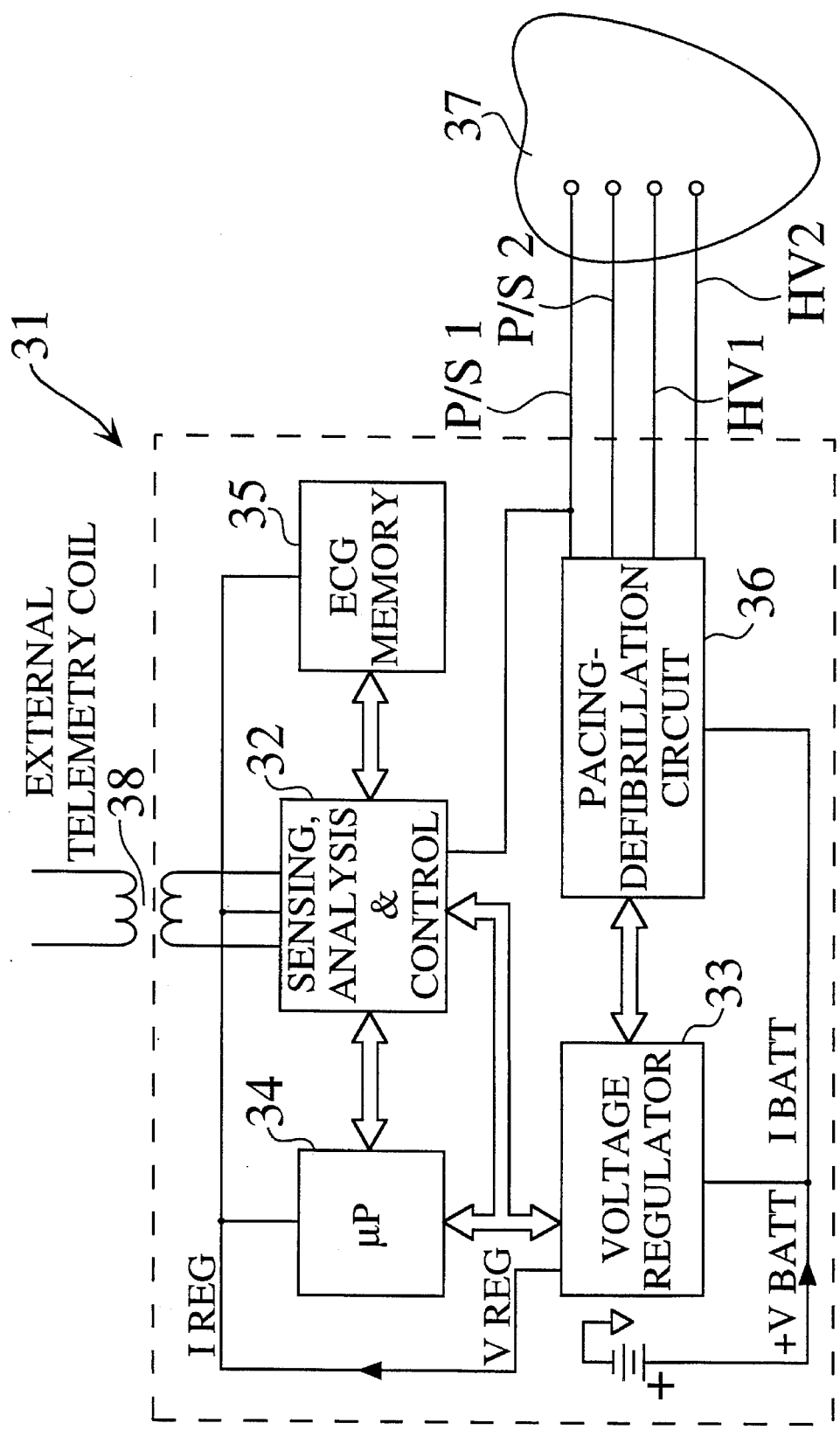
FIG. 2 is a block diagram illustrating the general organization of an implantable defibrillator-pacemaker system, employing a defibrillation method according to the present invention.

FIG. 2 provides a block diagram showing the general organization of an implantable combined defibrillator-pacemaker system 31. The system 31 includes sensing, analysis and control circuitry 32, a voltage regulator circuit 33 and an 8-bit microprocessor 34. A static random access memory (RAM) 35 is used to store digitized catracardiac electrogram (EGM) waveforms. External connections from a pacing-defibrillation circuitry 36 to the heart 37 are provided by two high voltage (HV) conductors HV1 and HV2, and a pair of pace/sense conductors P/S1 and P/S2 through which millivolt level EGM signals are sensed and which also carry pacing pulses to the heart 37. In a preferred embodiment at least conductors HV1, P/S1 and P/S2 are enclosed within a single lead, while conductor HV2 may be optionally contained within that same lead.

Telemetry to and from an external programmer is carried via a coil-to-coil link 38. System software within the microprocessor 34 determines whether the EGM parameters indicate an arrhythmia and, if so, the appropriate therapy is initiated. The raw EGM data can also be stored in memory 35 for later retrieval, or it can be telemetered out of the system 31 in real time. The general operation of one exemplary embodiment of the system 31 is described in U.S. Pat. No. 5,111,816 to Pless et al., which is incorporated herein by reference in its entirety.

Figure 3:
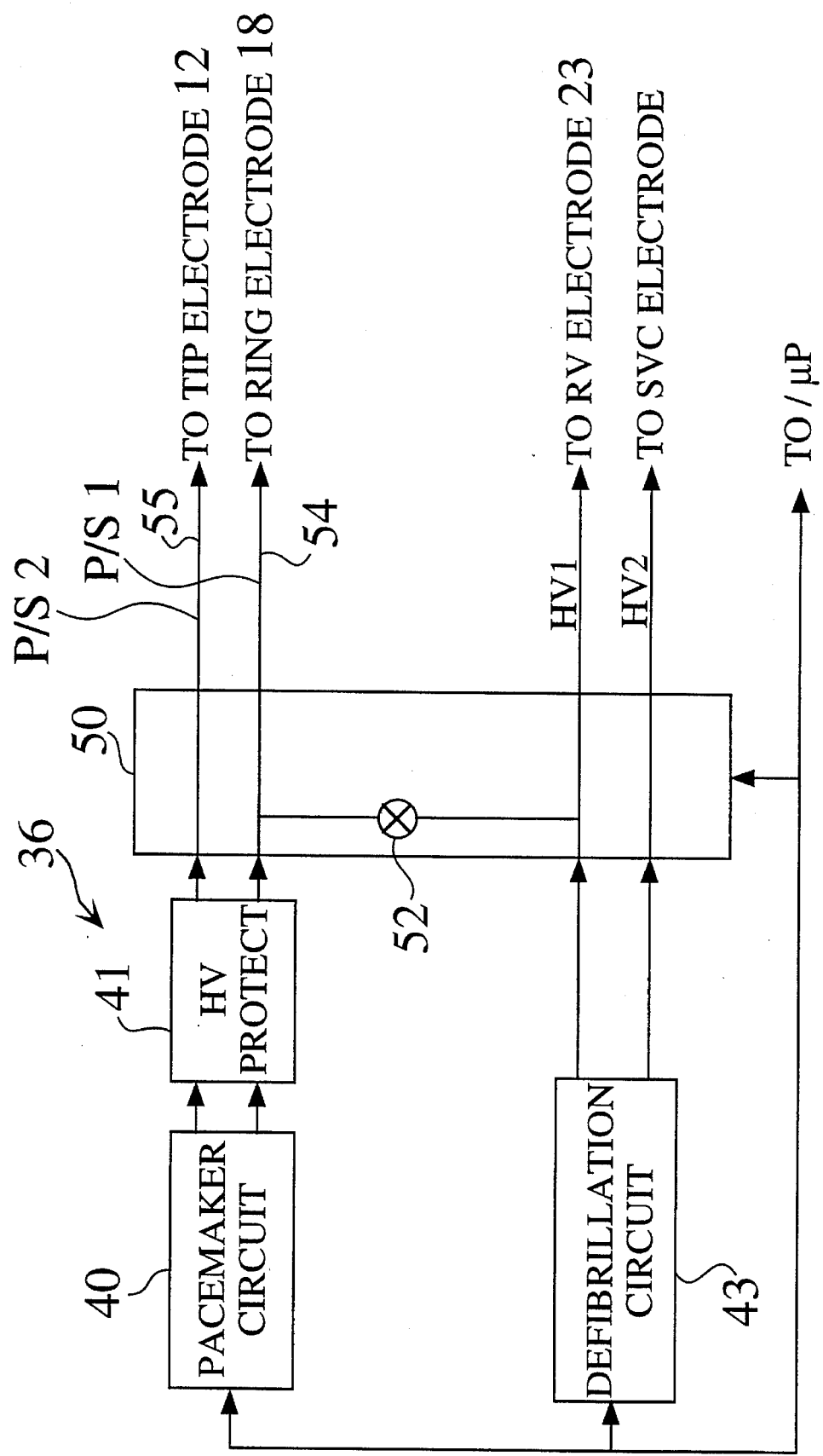
FIG. 3 is a simplified block diagram illustrating one embodiment of a pacing-defibrillation circuit, which forms part of the defibrillator-pacemaker system of FIG. 2, and which includes the switching matrix of the present invention.

FIG. 3 shows a block diagram embodiment of the pacing-defibfillation circuit 36 in accordance with the present invention, without its full complement of cardiac leads and electrodes. The heart 37 is defibrillated by high voltage therapy (i.e., pulses or shocks) which are delivered through the high voltage conductors HV1 and HV2 through their respective defibrillation electrodes, including a right ventricle (RV) defibrillation electrode and a superior vena cava (SVC) defibrillation electrode. As used herein, "high voltage therapy" can include defibrillation or cardioversion high voltage therapy, as well as lower sequentially delivered therapies. One embodiment of a defibrillation electrode is shown in FIG. 1 as the elongated high surface area electrode 23. Other exemplary defibrillation electrodes that can be used in conjunction with the present system 31 are illustrated in U.S. Pat. No. 5,014,696 to Mehra, which is incorporated herein by reference in its entirety.

For illustration purpose and without intention to limit the scope of the present invention, the pacing-defibrillation circuit 36 shows lead 10 to include the pacing/sensing conductor PS/2 as conductor 55 for connection to the tip electrode 12 and pacing/sensing conductor PS/1 as conductor 54 for connection to the ring electrode 18. In such an embodiment, the high voltage conductor HV2 is connected to the superior vena cava electrode (not shown in FIG. 1).

The pacing-defibrillation circuit 36 includes pacemaker circuit 40, high voltage protection circuit 41, and defibrillation circuit 43, whose general functions and circuit components are described in U.S. Pat. No. 5,111,816 to Pless et al., and U.S. Pat. No. 4,830,006 to Haluska et al. which is incorporated herein by reference in its entirety.

A switching matrix 50 forms part of the pacing-defibrillation circuit 36 and provides an external switching control between the various electrodes according to the defibrillation process of the present invention. Such defibrillation process is controlled by a special software program in the microprocessor 34. The switching matrix 50 includes at least one normally open switch 52 between the high voltage conductor HV1 and the ring electrode conductor 54.

Figure 4:
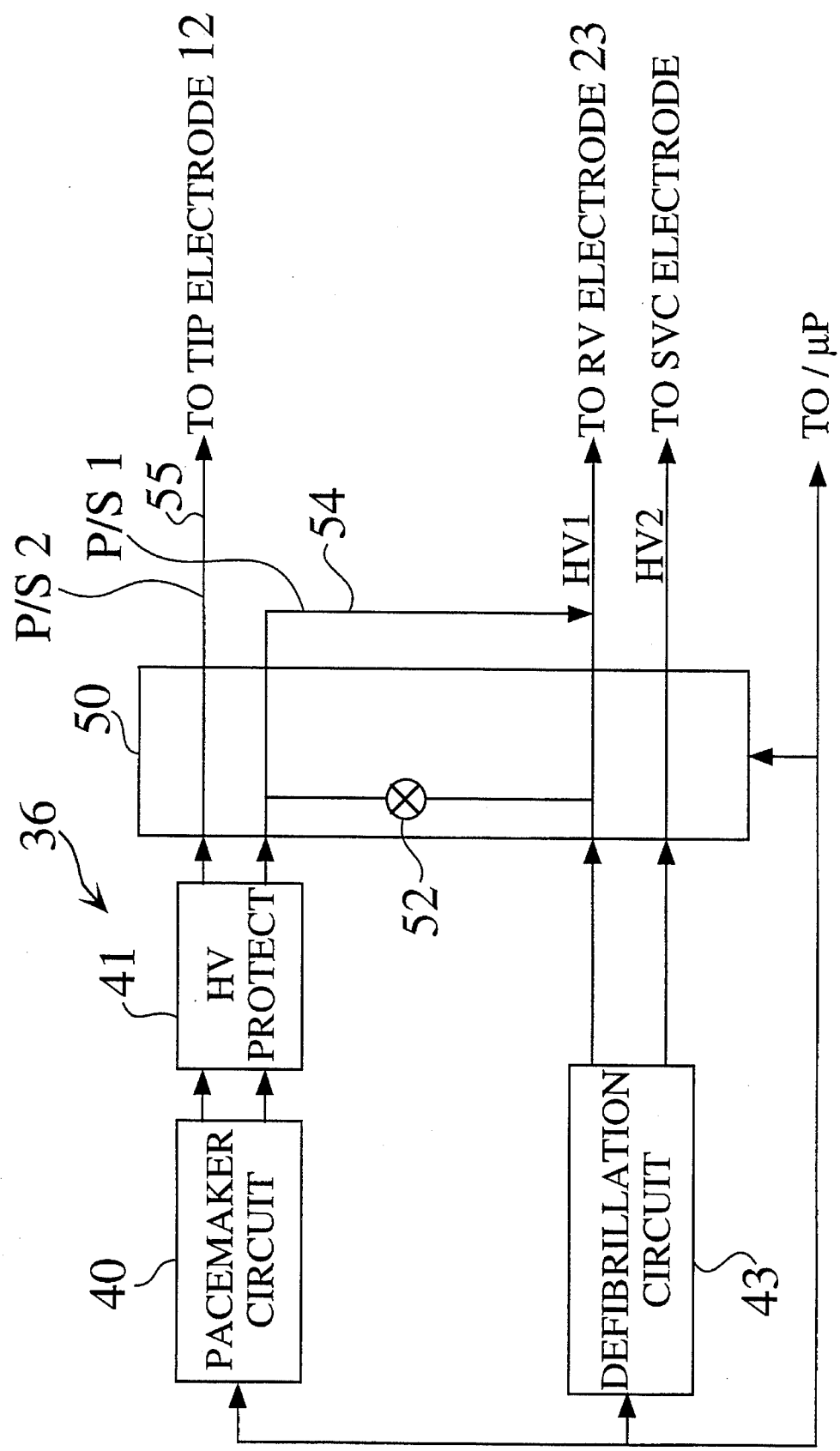
FIG. 4 shows another embodiment wherein the lead uses an integrated sensing mode, and the switch connects the defibrillation electrode to the tip electrode.

FIG. 4 shows another embodiment wherein lead 10 uses an integrated sensing mode. When closed, switch 52 connects defibrillation electrode 23 to tip electrode 12.

Figure 5:
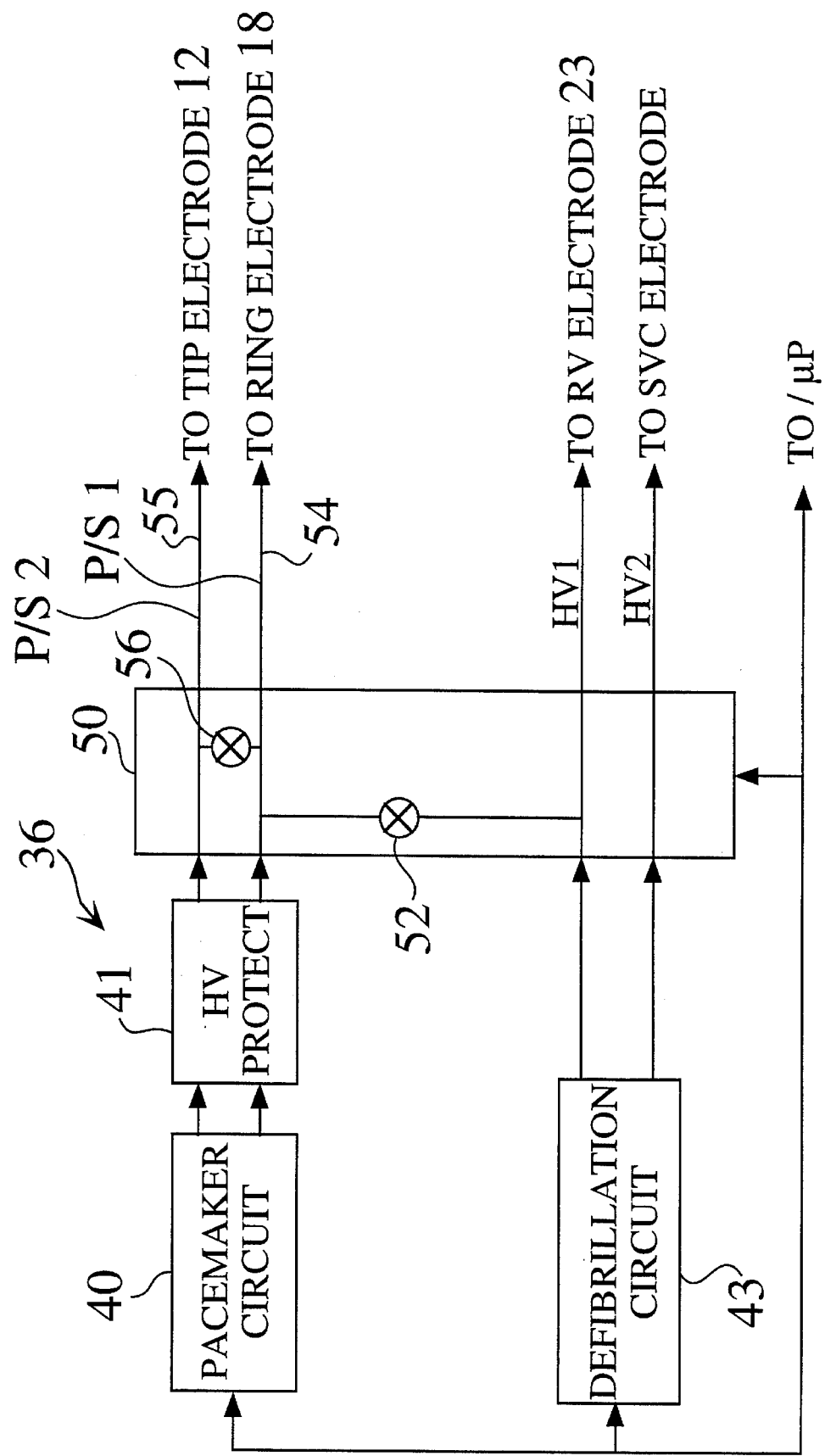
FIG. 5 is a simplified block diagram illustrating an embodiment of a pacing-defibrillation circuit, which forms part of the defibrillator-pacemaker system of FIG. 2, and which includes the switching matrix of the present invention.

FIG. 5 shows yet another embodiment having a normally open switch 56 that can be connected between the pacing/sensing conductors 54 and 55 during defibrillation, such that both the ring electrode 18 and the tip electrode 12 are activated, thus further shifting the effective position of the defibrillation electrode toward the heart apex.

Figure 6:
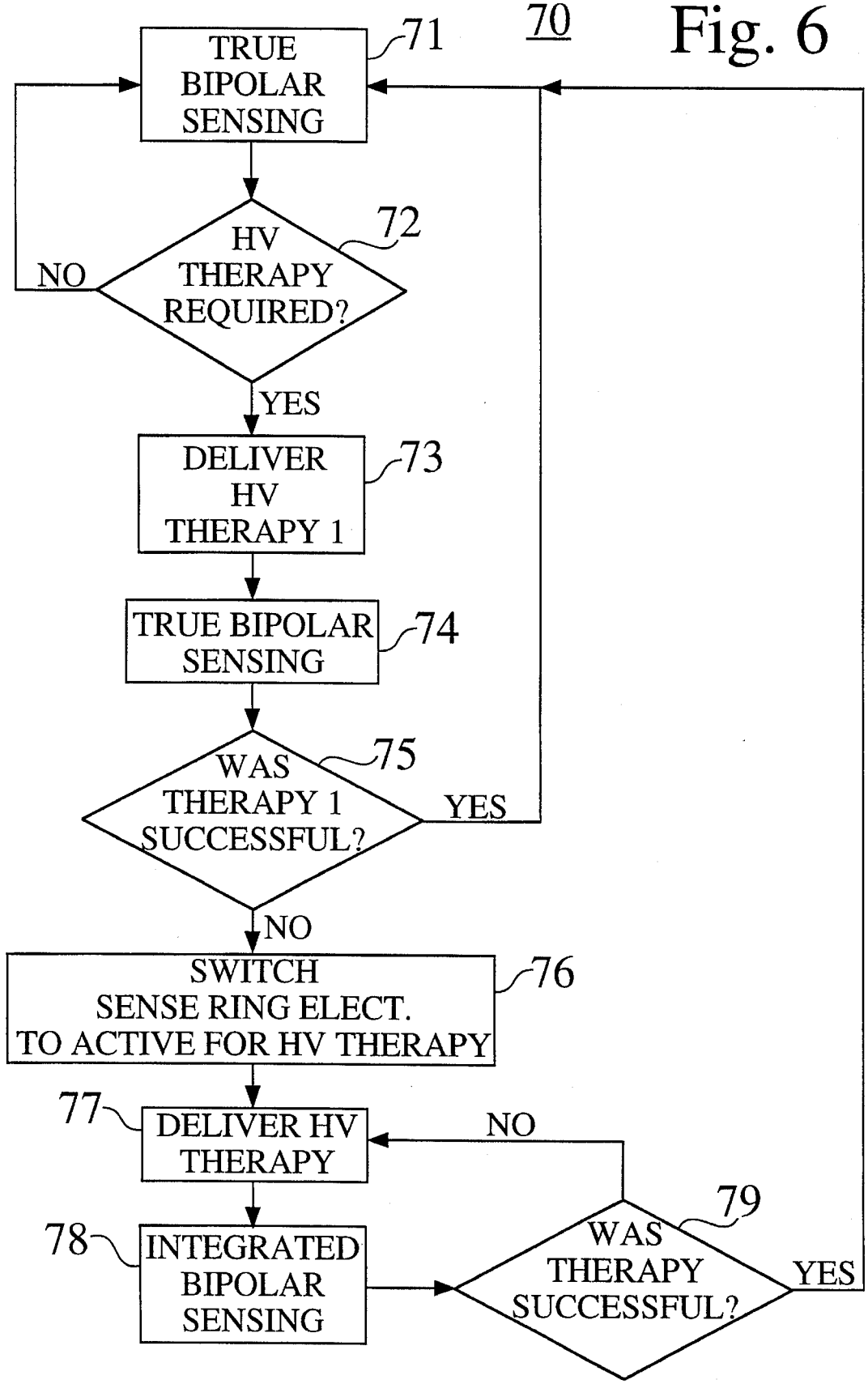
FIG. 6 is a flow chart illustrating a first embodiment of the defibrillation method as processed by the defibrillator-pacemaker system of FIG. 2.

Turning now to FIG. 6, a flow chart illustrates a first embodiment of the defibrillation method 70 as processed by the combined defibrillator-pacemaker system 31 of FIG. 2. As shown in steps 71 and 72, the system 31 would normally be operating in a true bipolar sensing mode as long as high voltage therapy is not required. If, however, high voltage therapy is determined to be needed, then, as shown in step 73, a first high voltage therapy (i.e., a shock or a pulse) is delivered via the defibrillation electrode 23.

True bipolar sensing is then carried out at step 74, and a determination is made at step 75, as to whether the first high voltage therapy was successful, and the heart 37 has restored to its normal sinus rhythm If this therapy is deemed to be successful, then system 31 resumes true bipolar sensing at step 71. If, on the other hand, the therapy was not successful, the switching matrix 50, under the control of the microprocessor 34, causes the switch 52 to close, thereby electrically connecting the defibrillation electrode 23 and the ring electrode 18, before the delivery of the subsequent high voltage therapy.

The inclusion of the ring electrode 18 as part of the effective area of the defibrillation electrode advantageously provides a defibrillation electrode which is effectively located in a more apical position and has an increased surface area. Another high voltage therapy is then delivered at step 77. While the preferred embodiment of the present invention includes the delivery of only one high voltage therapy, it should be understood to those with ordinary skill in the art that the microprocessor controller for the switching matrix 50 can be programmed to deliver successive high voltage therapies, i.e., one or more high voltage therapies, until a determination is made to "activate" the ring electrode 18 at step 76. In other words, the device may be programmable such that ring electrode 18 does not become active for defibrillation until after two or more failed shocks, the number depending on what is programmed.

Integrated bipolar sensing is then carried out at step 78, whereby the large surface area defibrillation electrode 23 and the coupled ring electrode 18 act, in connection with the tip electrode 12, as a sensing electrode. Based on this integrated bipolar sensing, a determination is made at step 79 as to whether the high voltage therapy delivered at step 77 was successful. If it is determined that this therapy was not successful, then another high voltage therapy is delivered at step 77, and the routine of inquiring about the success of the therapy (step 79), delivering a high voltage therapy (step 77) and conducting integrated bipolar sensing (step 78) is repeated as many times as necessary. Practically, this sequence is repeated about three to six times before terminating the defibrillation process 70. If, on the other hand, it is determined that the high voltage therapy was successful, then the switching matrix 50 is caused by the microprocessor 34 to switch back to and resume true bipolar sensing at step 71. By limiting the "activation" of the bipolar sense electrode for high voltage defibrillation to those situations where the initial high voltage therapy, which was delivered at step 73, has failed, the problem of residual charge at the metal-tissue interface remaining on the sense electrode occurs only after the initial rescue therapy (step 73).

Figure 7:
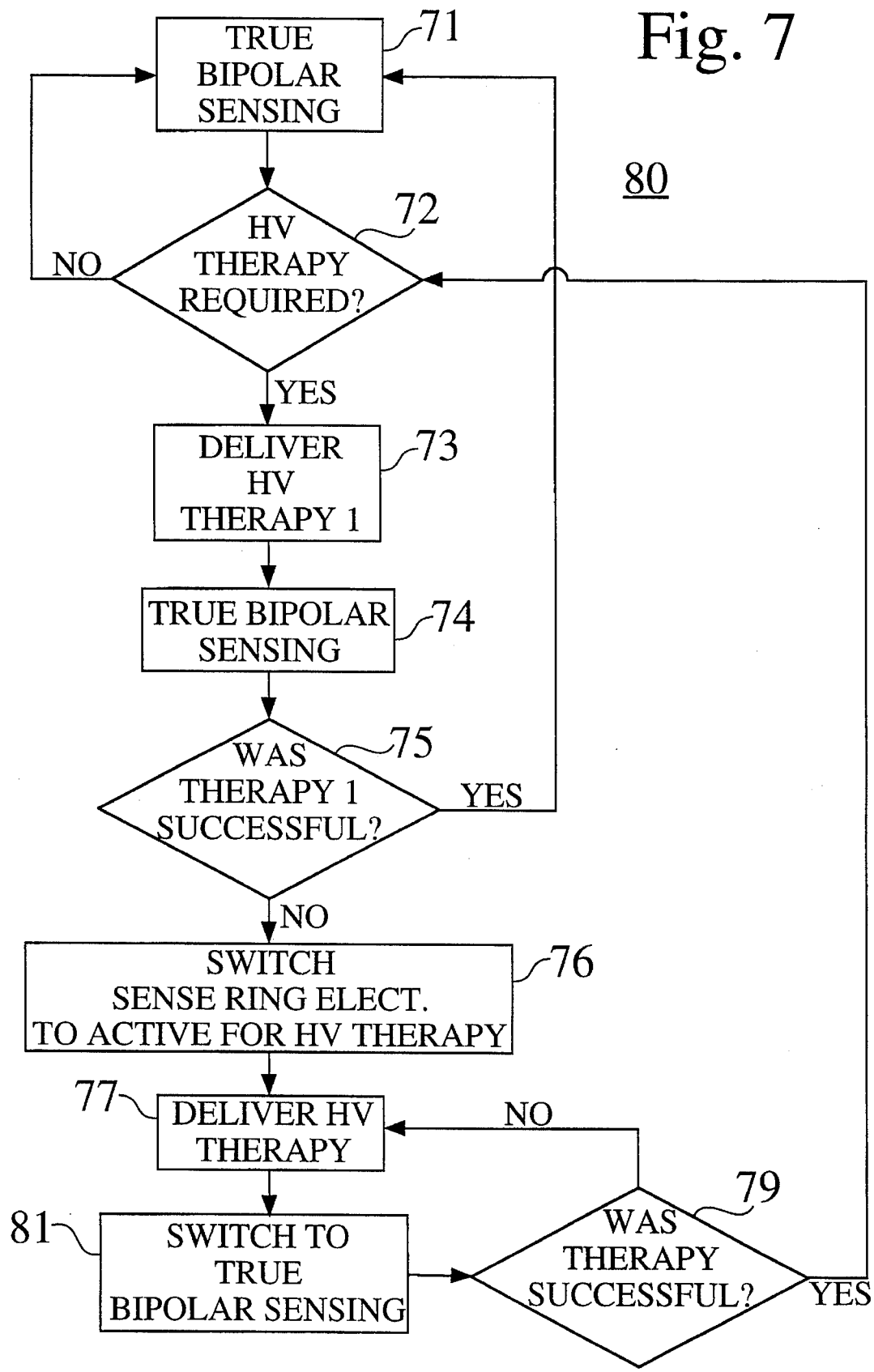
FIG. 7 is a flow chart illustrating a second embodiment of the defibrillation method as processed by the defibfillator-pacemaker system of FIG. 2.

FIG. 7 is a flow chart illustrating a second embodiment of the defibrillation method 80 as processed by the combined defibrillator-pacemaker system 31 of FIG. 2. The defibrillation method 80 of FIG. 5 is substantially identical to the defibrillation method 70 of FIG. 4, with similar reference numerals indicating similar or identical steps. The defibrillation method 80 differs from the defibrillation method 70 in that step 81 replaces step 78, whereby after the delivery of the high voltage therapy at step 77, the switching matrix is caused to switch back to true bipolar sensing (step 81) under the control of the microprocessor 34, by opening the switch 52; and further that if the result of the determination at step 79 is negative, i.e., the therapy was not successful, then the bipolar sense electrode is activated once again at step 76.

The foregoing description of the preferred embodiments has been presented for purposes of illustration and description. It is not intended to be exhaustive or to limit the invention to the precise forms described. Various modifications of the system components and methods of operation may be employed in practicing the invention. It is intended that the following claims define the scope of the invention, and that the structures and methods within the scope of these claims and their equivalents be covered thereby.

What is claimed is:

1. A method for delivering high voltage therapy to a patient's heart using a defibrillator connected to one or more leads having at least a first defibrillation electrode coupled to the defibrillator via a first high voltage conductor, a first sense electrode coupled to the defibrillator via a first sense conductor, and a second sense electrode coupled to the defibrillator via a second sense conductor, the method comprising the steps of:

(a) sensing electrical signals in a true bipolar sensing mode between the first and second sense electrodes;

(b) when required, delivering a first high voltage therapy between at least the first defibrillation electrode and a second defibrillation electrode;

(c) determining whether said first high voltage therapy was successful;

(d) if said first high voltage therapy was not successful then electrically connecting the first sense conductor to the first high voltage conductor; and (e) delivering a second high voltage therapy between at least the first sense electrode/first defibrillation electrode and the second defibrillation electrode.

2. The method according to claim 1, further including the step after step (e) of:

(f) sensing electrical signals in an integrated bipolar sensing mode between the first sense electrode/first defibrillation electrode and the second sense electrode.

3. The method according to claim 2, further including the steps of:

(g) determining whether said second high voltage therapy was successful; and (h) resuming true bipolar sensing if said second high voltage therapy was successful.

4. The method according to claim 3, further including the steps of:

(i) delivering a third high voltage therapy between at least the first sense electrode/first defibrillation electrode and the second defibrillation electrode if said second high voltage therapy was unsuccessful; and (j) following delivery of the third high voltage therapy, sensing electrical signals in an integrated bipolar sensing mode between the first sense electrode/first defibrillation electrode and the second sense electrode.

5. The method according to claim 1 and further including the step after step (e) of:

(f') electrically disconnecting the first sense conductor from the first high voltage conductor to allow true bipolar sensing.

6. The method according to claim 5, further including the steps after step (f') of:

(g') determining whether said second high voltage therapy was successful;

(h') electrically connecting the first sense conductor to the first high voltage conductor if said second high voltage therapy was not successful;

(i') delivering at least a third high voltage therapy; and (j') electrically disconnecting the first sense conductor from the first high voltage conductor to allow true bipolar sensing.

7. The method according to claim 1, and further including the step of causing the first and second sense conductors to be electrically coupled to each other after step (c) and prior to step (e), whereby high voltage therapy is delivered between at least first sense electrode/second sense electrode/first defibrillation electrode and second defibrillation electrode in step (e).

8. A method for delivering high voltage therapy using a defibrillator connected to one or more leads having at least a first defibrillation electrode coupled to the defibrillator via a first high voltage conductor, a first sense electrode coupled to the defibrillator via a first sense conductor, and a second sense electrode coupled to the defibrillator via a second sense conductor, the method comprising the steps of:

(a) sensing cardiac electrical signals in a true bipolar sensing mode between the first and second sense electrodes;

(b) if a first high voltage therapy is required then causing the first sense conductor to be electrically coupled to the first high voltage conductor; and (c) delivering a high voltage therapy between at least the first sense electrode/first defibrillation electrode and a second defibrillation electrode.

9. The method according to claim 8, further including the step (d) of electrically decoupling the first sense conductor from the first high voltage conductor after said step (c) and resuming true bipolar sensing.

10. The method according to claim 8, further including the steps of:

(d') after said step (c), sensing in an integrated bipolar sensing mode to determine whether said high voltage therapy was effective;

(e') if said high voltage therapy was effective, sensing in said true bipolar sensing mode; and (f') if said high voltage therapy was not effective, delivering a second high voltage therapy between at least the first sense electrode/first defibrillation electrode and the defibrillation electrode.

11. In a pulse generator system for sensing electrical signals from a patient's heart and for delivering defibrillating shocks to the patient's heart, the system including a lead having a ring electrode and a tip electrode for sensing and a first defibrillation electrode, a pulse generator comprising:

a sensing circuit electrically connected to the tip electrode and ring electrode;

a defibrillation circuit electrically connected to the first defibrillation electrode;

a second defibrillation electrode electrically connected to the defibrillation circuit;

a normally open switch connected between said ring electrode and said defibrillation electrode; and a processor for controlling said switch whereby said switch may be closed under control of said processor at the time a defibrillation shock is delivered to said patient's heart.

12. The pulse generator system of claim 11 and further including a pacing circuit for delivering pacing pulses through the tip electrode.

13. The pulse generator system of claim 11, said pulse generator further including a second switch electrically coupled between said ring electrode and said tip electrode, said second switch being controlled by said processor whereby said second switch may be closed under control of said processor at the time a defibrillation shock is delivered to said patient's heart.

14. A pulse generator system for sensing electrical signals from a patient's heart and for delivering defibrillating shocks to the patient's heart, the system including a lead having a tip electrode for sensing and two defibrillation electrode, at least one of said electrode on said lead, a pulse generator comprising:

a sensing circuit electrically connected to the tip electrode and the first defibrillation electrode;

a defibrillation circuit electrically connected to the first defibrillation electrode;

a second defibrillation electrode electrically connected to the defibrillation circuit;

a normally open switch connected between said first defibrillation electrode and said tip electrode; and a processor for controlling said switch.

15. The pulse generator system of claim 14 and further including a pacing circuit for delivering pacing pulses through the tip electrode.

16. A pulse generator for connection to an implantable lead in order to detect and manage cardiac arrhythmias, comprising:

a sensing circuit;

a defibrillation circuit;

a lead switching matrix having first and second sense conductors connected to said sensing circuit, at least first and second high voltage conductors connected to said defibrillation circuit, and at least one normally open switch between said high voltage conductor and said first sense conductor; and a controller for controlling operation of said switch.

17. The pulse generator according to claim 16, further including a second switch between said first and second sense conductors and operable by said controller for coupling and decoupling said first and second sense conductors.

* * * * *